United States Patent [19]
Laswick et al.

[11] Patent Number: 5,520,170
[45] Date of Patent: May 28, 1996

[54] AUTOMATIC RESUSCITATOR

[75] Inventors: Ronald A. Laswick, Brampton; Kevin D. J. Bowden, Orangeville, both of Canada

[73] Assignee: O-Two Systems International Inc., Mississauga, Canada

[21] Appl. No.: 328,767

[22] Filed: Oct. 27, 1994

[30] Foreign Application Priority Data

Oct. 29, 1993 [CA] Canada .................................... 2102070

[51] Int. Cl.$^6$ ........................ A61M 16/00; A61M 16/20; A62B 7/04
[52] U.S. Cl. ................ 128/204.18; 128/204.25; 128/205.24
[58] Field of Search ........................ 128/204.18, 204.25, 128/204.26, 205.24, 205.25

[56] References Cited

U.S. PATENT DOCUMENTS

| | | | |
|---|---|---|---|
| 2,865,368 | 12/1958 | Sanborn | 128/204.25 |
| 3,717,147 | 2/1973 | Flynn | 128/204.25 |
| 3,853,105 | 12/1974 | Kenagy | 128/205.24 X |
| 4,197,842 | 4/1980 | Anderson | 128/203.12 |
| 4,436,090 | 3/1984 | Darling | 128/204.26 |
| 4,437,461 | 3/1984 | Greenberg | 128/205.24 |
| 4,651,731 | 3/1987 | Vicenzi et al. | 128/204.25 |
| 4,682,591 | 7/1987 | Jones | 128/204.25 |
| 4,905,688 | 3/1990 | Vicenzi et al. | 128/204.21 |
| 5,211,170 | 5/1993 | Press | 128/204.18 |

*Primary Examiner*—Edgar S. Burr
*Assistant Examiner*—Eric P. Raciti

[57] ABSTRACT

An automatic resuscitation apparatus for administering a breathable gas to a patient that can be held in one hand, and containing the necessary valves and controls, and operable in automatic mode, demand mode, and manual mode, and having, a flow chamber for a breathable gas, a patient mask connector at an outlet of said flow chamber, a chamber valve within the flow chamber for permitting passage of breathable gas from the chamber to the mask connector, a exhaust for exhausting exhaled breath exteriorly of the flow chamber, a breathable gas supply to the flow chamber, a supply valve operable to provide an on-off control of the breathable gas supply, and, a timing valve responsive to flow of gas to the flow chamber, to move at predetermined intervals between on/off positions, the timing valve being connected to the supply valve, so as to procure on-off operation of the supply valve in timed relation to the timing valve.

10 Claims, 10 Drawing Sheets

AUTOMATIC RESUSCITATOR

FIELD OF THE INVENTION

The invention relates to a resuscitator apparatus for administering breathable gas to a patient. The apparatus is operable in three different modes namely an automatic timed mode, a demand response mode, and a manual mode. The apparatus with all valves and controls, is self contained within a small, compact, hand held unit.

BACKGROUND OF THE INVENTION

A wide variety of different breathing devices and resuscitators have been proposed, and many have been made. The simplest consist merely of a hand held mask with a manual valve. Usually a separate control unit was required for supplying gas to the mask.

Note complex units are known in which two or even three different modes of operation are possible. Again in these units the controls, for controlling the different modes, as well as the final gas pressure reducer were located in a separate component assembly and were not part of the mask patient valve assembly itself.

In the majority of even the more complex units the problem of changing over from one mode to the other in an emergency situation has involved various difficulties. Personnel must be highly trained, and must be capable of operating the unit with both hands at once, one on the mask and one on the control. These factors may interfere with the most effective use of the equipment. It will also be understood that such equipment will desirably be made available at locations where personnel may be less than adequately trained. Indeed, it is in just those hazardous locations i.e. remote from paramedic assistance, that emergencies are most likely to occur.

Clearly, it is desirable to provide such apparatus which is automatic in nature and which can be held and operated and controlled in one hand with both hands being able to remain on the mask/patient valve assembly and the patient so as to secure the mask to the patient in order to provide support to the jaw and, maintaining the patient airway, whilst creating an effective mask-to-face seal to reduce the potential for leaks at this junction.

The task of designing such an apparatus of such complexity, to fit within the palm of the hand is clearly beset with many difficulties. However, the advantages which will flow from such a self contained easily operated apparatus are many.

In such an improved apparatus it would be desirable to eliminate the separation of the controls from the patient valve, and to develop a device which gives more stable performance than other devices on the market, and to provide automatic patient override of the automatic cycling circuit in the event that the patient commences spontaneous respiration and demand breathing. This has not been achieved in any other single resuscitator unit.

Clearly such improved apparatus could be made available to a much wider number of persons with a much lower degree of training thereby placing the apparatus at the locations where emergencies are most likely to arise and require immediate treatment.

The improved apparatus should be capable of operating in an entirely automatic timed mode, for treatment of a patient who is not breathing, and should be capable of changing from the automatic mode to a demand mode when a person commences a natural inspiratory effort, and should also preferably be capable having the automatic mode overridden by a manual control mode for use by a trained paramedic.

BRIEF SUMMARY OF THE INVENTION

With a view to satisfying the foregoing objectives, the invention comprises an automatic resuscitation apparatus for administering a breathable gas to a patient, which can be to hand held in one hand, and contains the necessary valves and which is controls, and operable in automatic mode, demand mode, and manual mode, and having, a flow body for a breathable gas, having a flow passage connecting to a valve chamber a patient mask connector at an outlet of the flow chamber, a chamber valve within the chamber for permitting passage of breathable gas from the chamber to the mask, exhaust openings for exhausting exhaled breath exteriorly of the flow body, a breathable gas supply for the flow body, a supply valve operable to provide an on-off control of the breathable gas supply, and, a timing valve responsive to flow of gas to the flow body, to move at predetermined intervals between on/off positions, the timing valve being connected to the supply valve, so as to procure on-off operation of the supply valve in timed relation to the timing valve.

A further feature of the invention includes a gas flow control port between the breathable gas supply and the mask connection.

A further feature of the invention includes further gas flow control ports for controlling flow of gas to the timer valve, so that the timer valve operates on a timed cycle responsive to flow of gas thereto.

A further feature of the invention provides a plurality of gas flow control orifices, and a control nozzle adapted to registered with a selected one of the orifices.

A further feature of the invention provides that the timer valve has a housing, a piston moveable to and fro within the housing, a valve connected to the piston, and a spring normally urging the piston in one direction, and being responsive to gas pressure to move against the spring, the valve being connected to the gas supply valve.

A further feature of the invention provides that the flow control port has a disk member, a plurality of first flow openings located spaced from one another on a part of the disk member, a plurality of flow restricting orifices in the disk member spaced apart from one another, respective ones of the flow openings and restricting orifices being arranged in opposition to one another along respective axes of the disk, a flow nozzle to register with one of the flow openings, a control nozzle adapted to register with one of the orifices, and lever for rotating said disk member relative to the nozzles.

A further feature of the invention in which the supply valve means has a housing, a piston moveable within the housing, a spring normally urging the piston in one direction, a gas opening in the housing supplying pressurized gas to the piston, causing it to move against the spring, and a valve connected to the piston and gas inlet and gas outlet conduits connected to the housing, and controlled by movement of the valve.

A further feature of the invention and including an outlet conduit connected to the supply valve for transmitting pressurized gas to the flow body, and also supplying pressurized gas to the timing valve, and a gas flow control port for controlling flow of gas from the supply valve to the timing valve.

A further feature of the invention including a demand valve connecting with the flow body, a demand gas flow conduit to supply gas to the demand valve, the demand valve being responsive to a predetermined drop in pressure in the flow body to open and to permit flow of gas into the chamber from the demand flow conduit.

A further feature of the invention and including a shut-off valve connected to the demand valve.

A further feature of the invention in which the exhaust openings formed around the patient mask connection, and in which the chamber valve has a generally annular wall portion, and an inner ring, and an annular diaphragm extending between the annular wall and the inner ring, for covering the exhaust openings, and further including a one-way outflow valve supported within the inner ring, and permitting flow of breathable gas from the flow body into the patient mask.

A further feature of the invention including a pressure relief valve communicating with the flow body, and a piston operable to hold the relief valve closed, during supply of breathable gas, and a spring normally urging said piston away from the valve, and operable, in the absence of gas pressure, to permit outflow of gases from the flow chamber.

A further feature of the invention including a shut-off valve communicating with the demand valve, and responsive to opening of the demand valve to supply gas pressure to the timing valve, so as to move it to its off position, closing the supply valve so that the timing valve and the supply valve are both shut off during operation of the demand valve.

The various features of novelty which characterize the invention are pointed out with more particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DESCRIPTION OF A SPECIFIC EMBODIMENT

Figure 1:
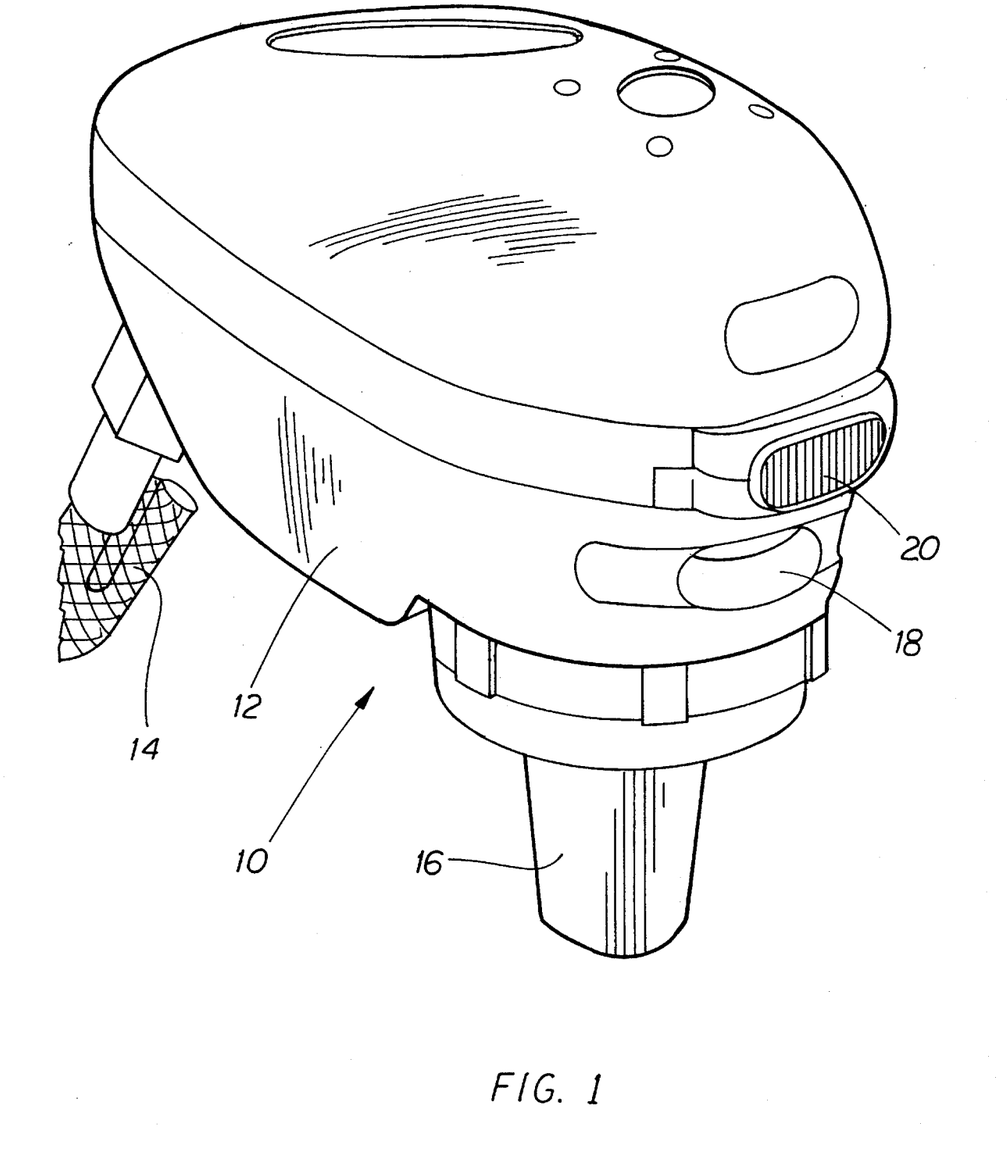
FIG. 1 is a perspective illustration of a resuscitation apparatus illustrating an embodiment of the invention.

As already explained above the embodiment illustrated here for the purposes of explaining the invention comprises a hand held resuscitation unit indicated generally as 10 which in turn comprises a smooth exterior body shell 12, a pressurized gas inlet coupling 14, and a reduced pressure breathable gas outlet connection 16 adapted to be connected to a typical face mask (not shown) of any suitable type such as are very well known in the art.

A timer control slider 18 extends from one end of the housing shell 12, and a manual control button 20 is located to adjacent the slider 18, for purposes to be described below.

The sizing and shape of the housing shell 12 are such that it may easily be grasped and held in one hand, with the control slider 18 and the manual button 20 being operable by the fingers of the one hand, ID this way the other hand is left free to assist in maintaining the patients airway clear, and in achieving a good mask-to-face seal.

Figure 2:
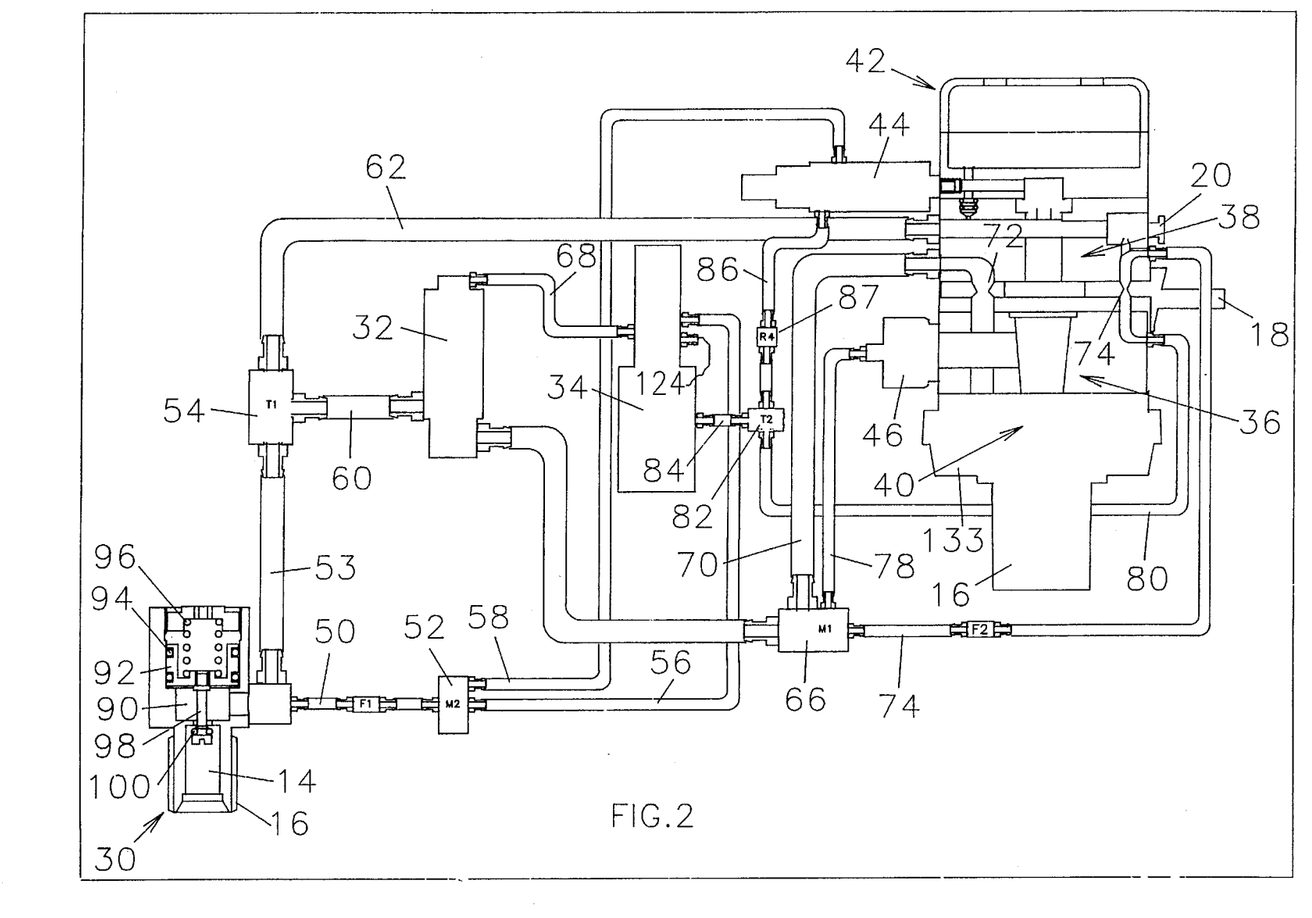
FIG. 2 is a schematic block diagram illustrating the main components of the resuscitator apparatus of FIG. 1.

Referring now to FIG. 2 it will be understood that this Figure illustrates in general schematic form the principle components located within the housing shell 12.

The principle components will be seen to comprises a pressure regulator 30, a main control switch 32, a timing shuttle valve assembly 34, a flow body 36, a flow control rotor 38, a diaphragm housing 40, a demand valve 42, an automatic shut-off valve 44, and an anti-lockup valve 46.

Again referring to FIG. 2, the pressure regulator 30 is adapted to be connected to a supply of pressurised breathable gas typically via a separate pressure reducer (not shown) such as a cylinder (not shown) by means of inlet coupling 14.

Gas from the pressure regulator 30 is supplied along a conduit 50 to a manifold 52, and gas is also supplied from the regulator 30 along conduit 53 to a second manifold 54.

The manifold 52 is connected to a first conduit 56, which is connected to the timing shuttle 34. Manifold 52 is also connected to a second conduit 58 which is connected to the auto shut-off valve 44.

The second manifold 54 is connected by conduit 60 to main switch 32, and by conduit 62 to the demand valve 42.

Main switch 32 is connected at one end by conduit 64 to a third manifold 66. Main switch 32, at its other end, is connected by conduit 68 to timing shuttle 34.

Third manifold 66 is connected by conduit 70 to a first nozzle 72 on one side of the flow control rotor 38 in flow body 36. Third manifold 66 is connected by conduit 74 to a second nozzle 76, located at a separate location on an opposite side of flow control rotor 38.

Manifold 66 is also connected by a third conduit 78 to anti-lockup valve 46.

Nozzle 76 is adapted to supply gas by means described below to a conduit 80. Conduit 80 connects with a manifold 82. Manifold 82 is connected by conduit 84 to timing shuttle 34.

Manifold 82 is also connected by a conduit 86 to auto shut-off valve 442, via flow restrictor 87

Gas filters 88 and 89 are located in conduits 50 and 74 to filter out any particles.

The various principle components will now be described in more detail, with reference to FIGS. 3, 4A and 4B, 5, 6 and 7A and 7B.

Pressure Regulator 30

The pressure regulator 30 (FIG. 2) comprises a pressure chamber 90 and a piston chamber 92, containing a piston 94 biassed by a spring 96. A valve spindle 98 carrying a valve such as an O-ring 100, extends to a piston to chamber 90.

Upon application of gas pressure to chamber 90, piston 92 will respond and rise, depending upon the pressure of spring 96. This will have the effect of drawing the O-ring 100 towards the entry to chamber 90, closing it off and shutting off flow of gas. By suitable adjustment of threaded ring 102, the pressure of spring 96 can be varied.

The details of such pressure regulators are generally speaking well known in the art, and require no further description.

The pressure regulator 30 operates to accept incoming relatively low pressurised gas via a pressure reducer (not shown) from a typical pressurised gas source, eg. a cylinder (not shown), and reducing the pressure further, down to a breathable gas pressure and regulating it to a constant pressure.

Regulator 30 is designed to maintain the internal circuit gas pressure within the unit in a stable state.

Main Switch 32

The main gas switch 32 (FIG. 3) comprises a valve chamber 104, and a piston chamber 106. Valve 108 is connected to piston 110. A spring 112 biasses piston 110 into an upper open position, Valve 108 normally opens conduit 60, so that gas can be supplied from the pressure regulator 30, through conduit 64, to flow body 36.

Figure 3:
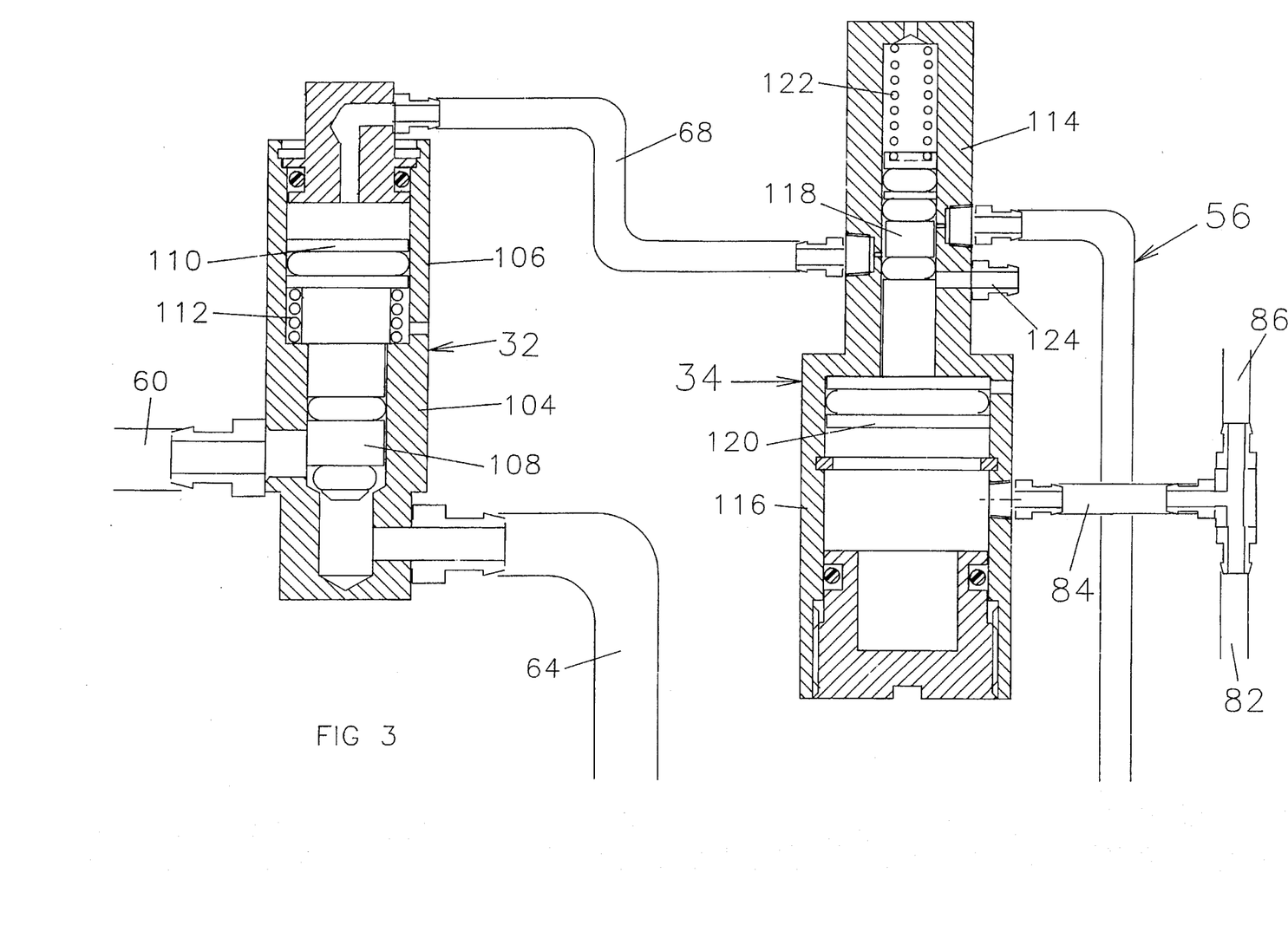
FIG. 3 is a sectional illustration of the timer shuttle, and the main gas supply valve.

However, upon gas pressure being applied through conduit 68 to piston 110, piston 110 will drive downwardly against spring 112 thereby sealing conduit 60, and preventing flow to conduit 64.

When the gas pressure from conduit 68 drops, the piston 112 moves upwardly thereby again releasing supply of gas from conduit 60 to flow into conduit 64.

Timing Shuttle 34

The timing shuttle 34 (FIG. 3) comprises an upper valve chamber 114, and a lower piston chamber 116.

A valve 118 in chamber 114 is connected to piston 120 in chamber 116.

The valve 118 is normally urged downwardly by spring 122.

Gas pressure from conduit 84 applied to piston 120 will cause valve 118 to move into its upper position, against spring 122. Absence of pressure in conduit 84 will permit the piston 120 to move downwardly, under the influence of the spring.

This upward and downward movement will alternately connect conduit 68, to the main switch 32, with conduit 56, or will communicate conduit 68 with ambient outlet 124 thereby releasing the pressure in conduit 68 and main switch 32.

It will thus be seen that the cycling of the timing shuttle piston 120 and valve 118 to and fro, will cause closing and opening of the piston 110 and valve 108 in main switch 32 thereby alternately supplying gas to conduit 64, and shutting off supply of gas to conduit 64, in a precisely timed manner.

When gas is supplied to conduit 64 it is in turn supplied to manifold 56 and conduit 70, and then to nozzle 72, thereby supplying breathable gas to flow body 36, through a flow opening (described below) in flow control rotor 38 (see FIG. 6).

Simultaneously however gas will also be supplied along the conduit 74 to the nozzle 76, where it passes through a much smaller orifice (described below) in flow control rotor 38 (FIG. 6) down through conduit 80 and manifold 82 and back to conduit 84, connected to timing shuttle 34 (FIG. 3).

The complete sequence of operations will be described below after describing the remaining principle components.

Flow Body 36

The flow body 36 (FIGS. 4A & 4B) comprises a generally cylindrical body 130, having at its lower end a moulded end member 132, enclosing a valve chamber 133 and defining exhalation ports 134, and in end member 132 mounted the patient mask connector 16. Ports 134 are closed by a one-way flapper valve 135.

Figure 4A:
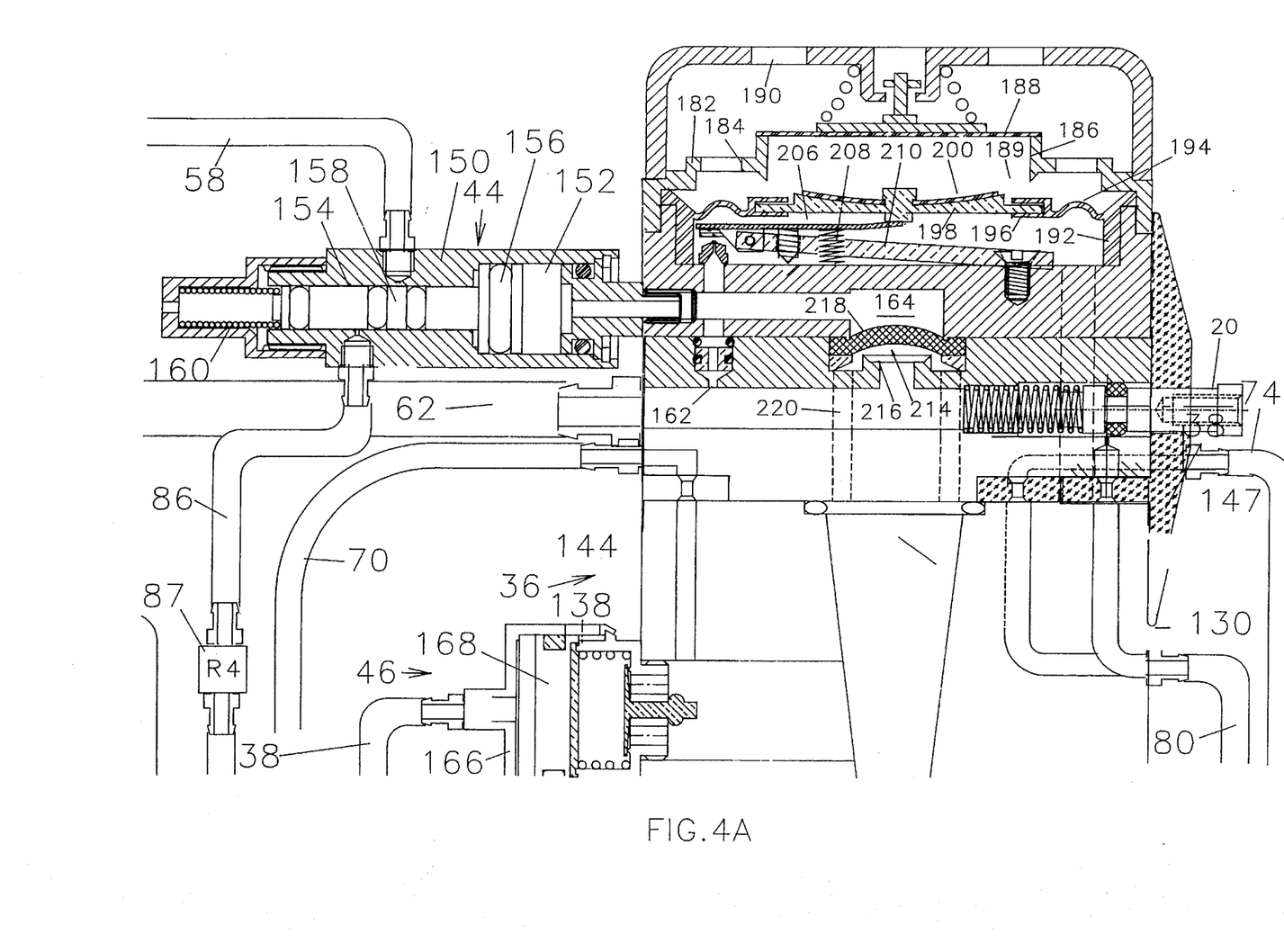
FIG. 4A is a vertical section of an upper portion of the flow body of FIG. 2.
Figure 4B:
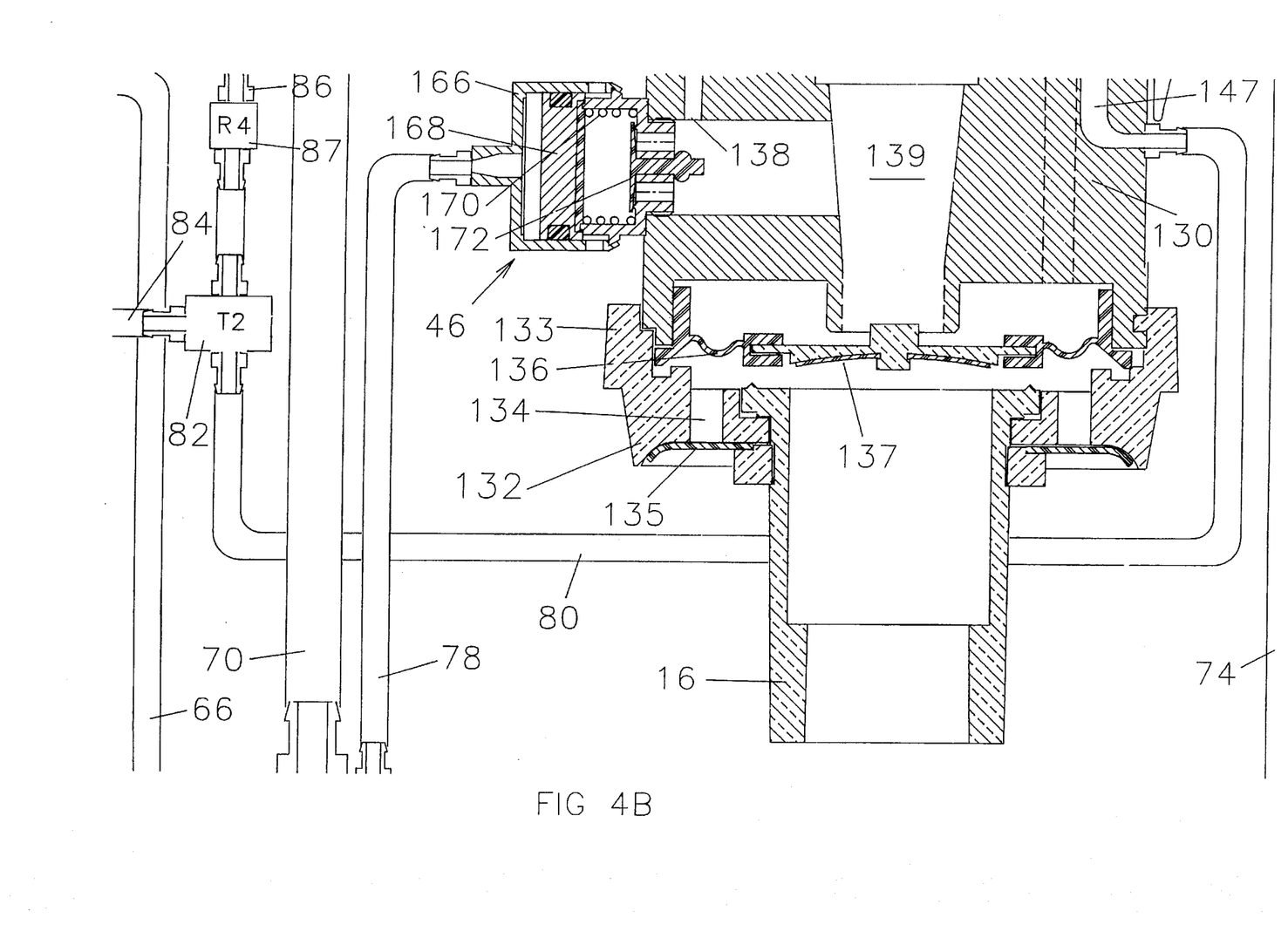
FIG. 4B is a vertical sectional of the lower portion of the flow chamber.

The end member 132 defines seating surfaces S for receiving a flexible diaphragm 136, which is adapted to close the ports 134, but which is naturally biassed to spring upwardly and open the ports 134 in the absence of any pressure within the housing body 130.

Diaphragm 136 supports a central supply flapper valve 137, closing registering openings in diaphragm 136, and which is adapted to flex downwardly upon the increase of pressure in housing body 130.

Body 130 defines a timed flow conduit 138, and a central demand flow conduit 139. Both conduits communicate with valve chamber 133.

In the automatic mode, breathable gas is supplied via nozzle 72, at timed intervals.

The demand and manual modes will take place in a different manner described below.

Within the body 130 there is provided the flow control rotor 38 already referred to. It comprises an exterior sleeve 140, and integrally formed therewith, an internal disk member 142. The manual slider 18, already referred to, is connected with the sleeve 140.

Figure 6:
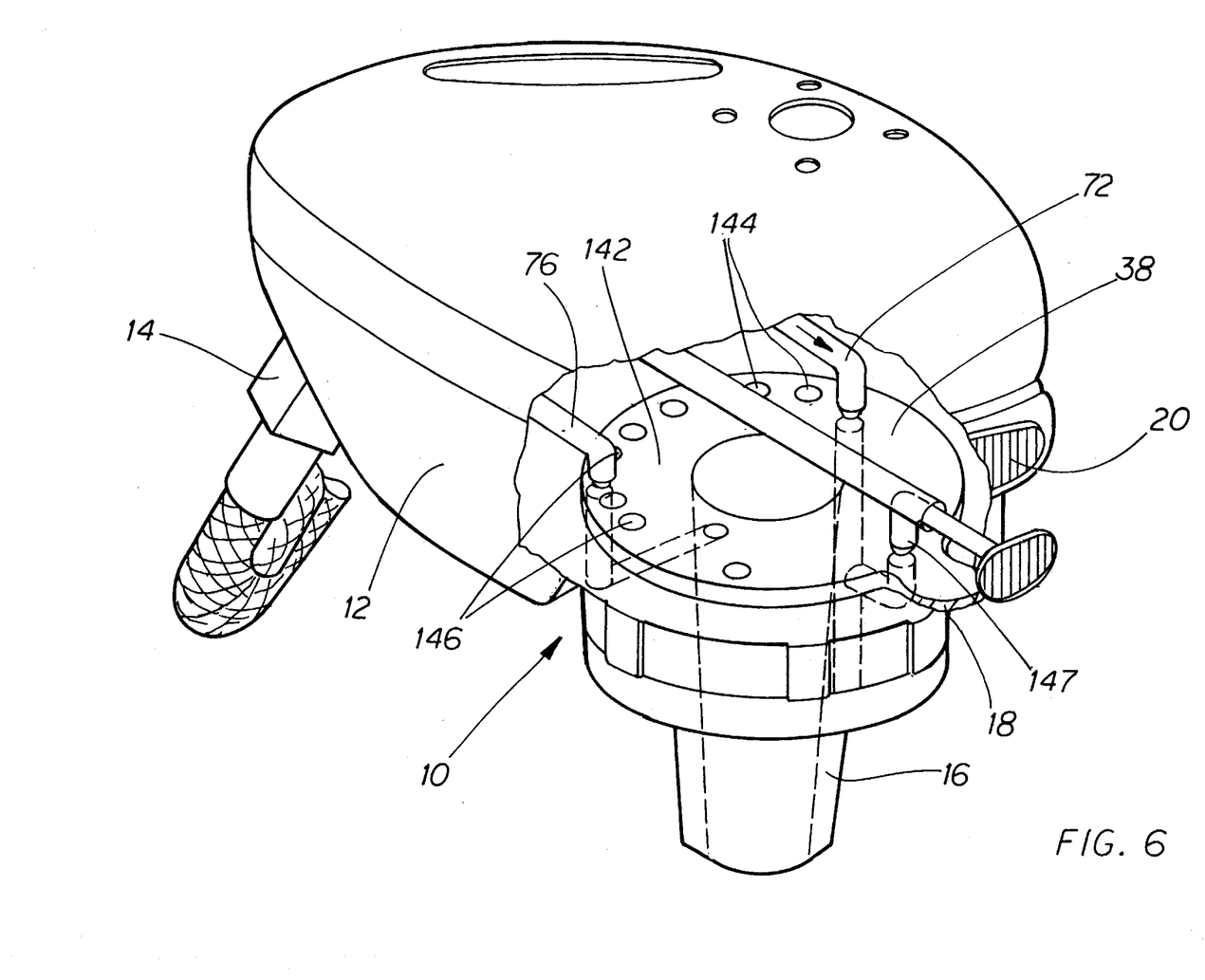
FIG. 6 is a perspective illustration of the resuscitation apparatus with a portion of the flow body and flow control partially cut away.

As best shown in FIG. 6 disk 142 is provided with a plurality of flow openings 144—144, and a plurality of timing control orifices 146—146.

Flow openings 144 are of varying diameter, to vary the gas flow to the patient, and a predetermined number, in this case six such flow openings, are provided, radially spaced apart.

A third nozzle 147 is located to register with a separate orifice (not shown) to operate in the manual flow mode described below. The timing control orifices 146 in this embodiment are only five in number, and vary in diameter from a larger size progressively to a smaller size, and are radially spaced apart.

The respective orifices 146 and flow openings 144 are located in pairs on radii of the disk 142, being spaced apart by equal angular SPACINGS, except for the sixth flow opening, which does not have a corresponding control orifice, for reasons to be described below.

By operation of the slider 18, the disk 142 can be rotated. In this way a selected one of control orifices 146 can be registered with nozzle 76, while at the same time the corresponding flow opening 144 will register with nozzle 72.

Nozzle 72 registers with conduit 138, and nozzle 76 registers with a bleed conduit 77 connecting with conduit 80.

Since the openings 144 and orifices 146 are of varying sizes, it will be seen that the flow rate of gas through any one pair of openings 144 and orifices 146 will be different from that of the flow through adjacent pairs of openings and orifices, for reasons to be described below.

Demand Valve 42

Figure 7A:
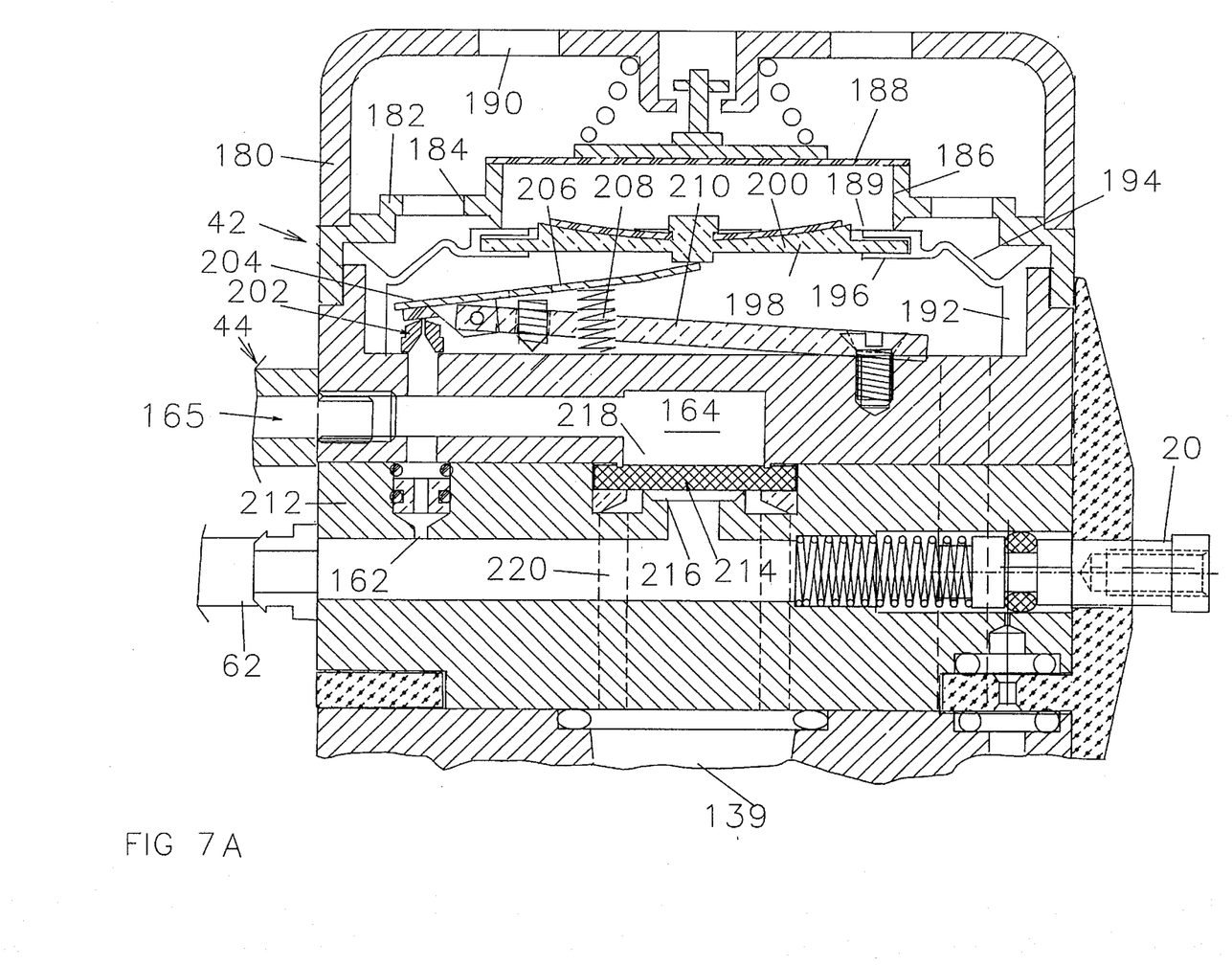
FIG. 7A is an enlarged section, corresponding to FIG. 4A, of the demand valve in a closed position.
Figure 7B:
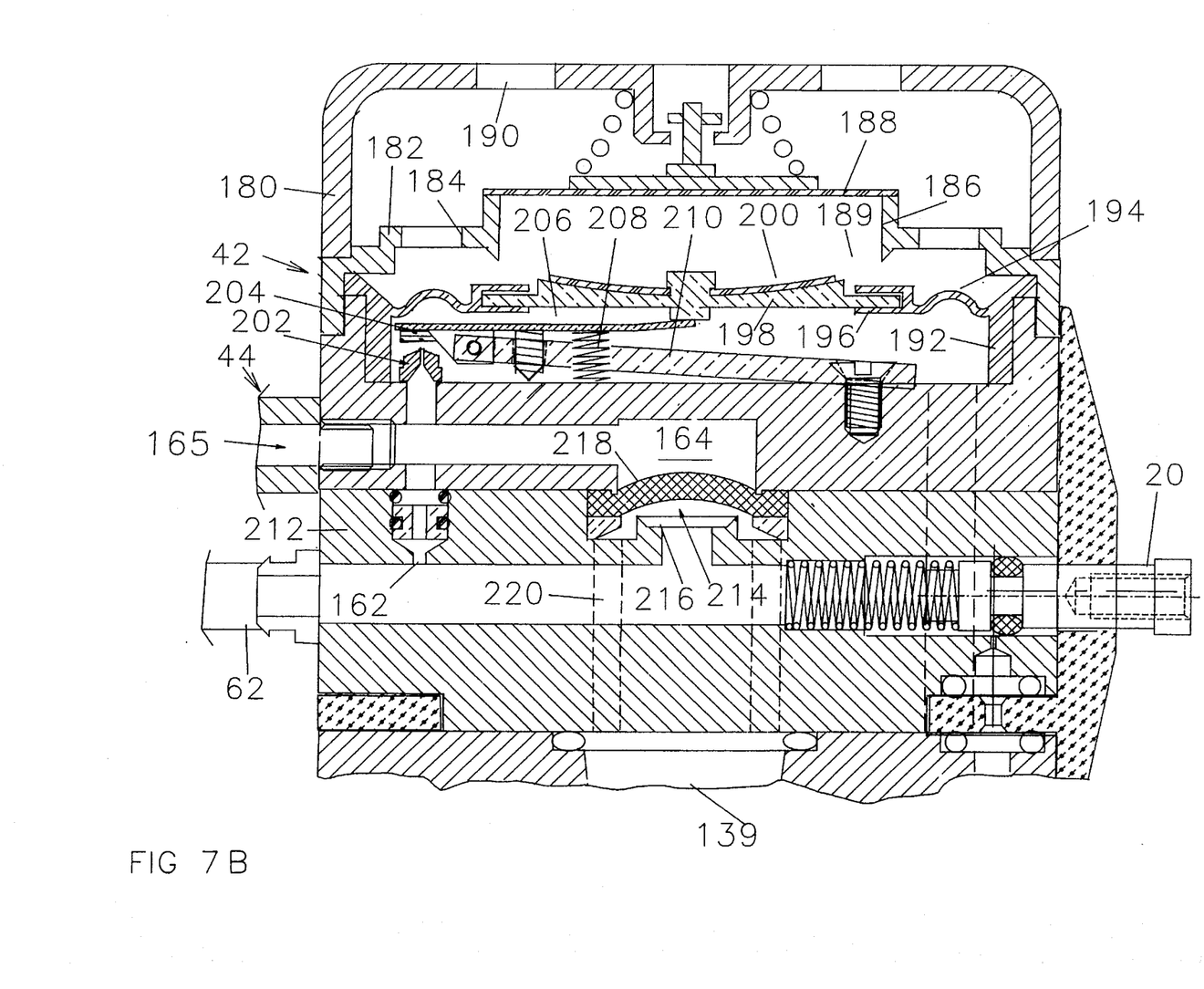
FIG. 7B illustrates the demand valve of FIG. 7A, in its "open" position.

The demand valve 42 is located in the upper end of housing 130 (FIGS. 4A, 7A and 7B). Such demand valves are of many different designs and are well known in the art. The demand valve 42 responds to inspiratory effort by the patient to admit breathable gas via conduit 62.

This therefore overrides the operation of the timing shuttle valve 34 and the main switch valve 32. Thus if during resuscitation, the patient commences inspiratory effort, this effort will not be interrupted by the operation of the timing shuttle 34 and the main switch 32, but can take place freely in response to the patients' own efforts.

The demand valve 42 also includes, in known manner, a pressure relief blow off valve, all of which are described below, in connection with FIGS. 7A and 7B.

Auto-Shut Off Valve 44

In order for the demand valve 42 to function independently of the timing shuttle 34 and the main switch 32, the auto shut-off valve 44 (FIG. 5) is provided which cooperates with the demand valve 42.

The auto shut-off valve 44 comprises a body 150 defining a piston chamber 152 and a valve chamber 154. A piston 156 is moveable within piston chamber 152 and a valve body 158 is moveable within valve chamber 154. A spring 160 normally urges the valve body 158 and the piston 156 to the right hand direction (as shown in phantom in FIG. 5). Conduit 62 connects via a bleed flow orifice 162, to conduit 163 and also to chamber 164 in demand valve 42. Gas pressure is thus applied to the piston 156, and urges it in the left hand direction against spring 160.

Figure 5:
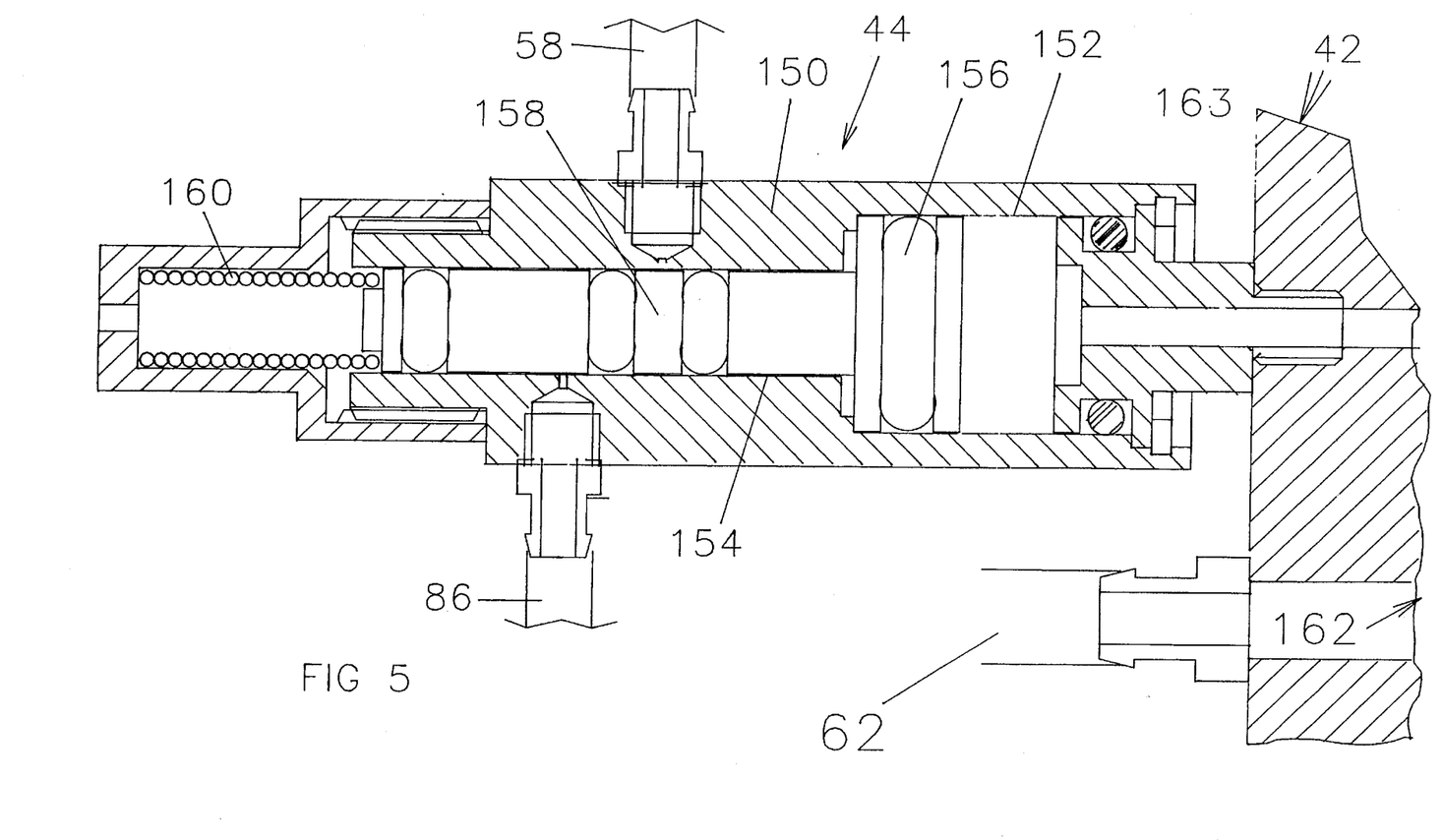
FIG. 5 is a section of the auto shut off valve along line 5—5 of FIG. 2.

Gas pressure is also applied continuously to valve body 158, by conduit 58, connected to manifold 52.

However, until a patient makes an inspiratory effort, the auto shut off valve 44 remains closed, by gas pressure applied to piston 156, from bleed orifice 162.

Once a patient makes an inspiratory effort, as may well happen during the automatic timed mode of operation, the pressure in the conduit 163 is decreased (as described below) by the flow of gas to the patient. This decrease in pressure occurs in piston chamber 152, allowing piston 156 with attached valve 158 to move to the right under spring pressure opening the auto shut off valve and allowing gas to flow from conduit 58 to conduit 86, and thus to manifold This will then have the effect of pressurizing the timing shuttle piston 120, to move upwardly against spring 122.

This will then allow gas to pass from conduit 56 through to conduit 68, to pressurize the piston 110 in the main switch 32.

This will then immediately shut off the timed pulses of gas supplied by conduit 64 and conduit 70 to the flow body, and will permit the patient to inspire gas supplied through conduit 62 and the demand valve 42, at will (as described below).

In the event that the patient ceases inspiratory effort, then the demand valve 42 will close (as described below), and the auto shut-off valve 44 will move to the left, thereby shutting off supply of gas from conduit 58 to conduit 86, and permitting the timing shuttle piston 120 to descend. This will then shut release pressure in main switch 32 via conduit 68 to ambient port 124 in timing shuttle 34. Main switch 32 will then open supplying gas to conduits 64 and 70, in a series of timed pulses.

It will thus be seen that the change over from automatic mode to demand mode, and the change over again from demand mode back to automatic mode is entirely automatic and independent of the intervention of the operator. All the operator has to do is to attend to the other needs of the patient such as maintaining the airway open, and ensuring that the mask-to-face seal is maintained, thereby excluding exterior air, or contaminants or even poisonous gases.

The manual control button 20 is illustrated in FIGS. 7A, and 7B. It will be seen that the manual control button 20 is located adjacent the slider 18, for convenience of operation. The manual control button 20 is connected to the demand supply conduit 62.

When using this mode of operation, the slider 18 will be rotated so that the nozzles 72 and 76 are shut-off, because they do not register with any of the openings 144 or orifices 146. In this mode of operation, the slider 18 is be rotated so that the third nozzle 147 is positioned to register with a separate orifice (not shown) located in flow disc 142 which will connect pressure in conduit 62 to conduit 80 to manifold 82 to 84, and thus to piston 120 in timing shuttle 34. This allows pressure from conduit 56 to pass to piston 110 in main switch 32, which closes off pressure from conduit 56 to conduit 60 to 64. This will thus disable the timing shuttle and the main switch operation, so that automatic timed operation cannot take place.

When the operator depresses manual button 20, manual button 20 releases pressure in conduit 80 to atmosphere which depressurises main switch piston 110 and allows gas to flow to conduit 64 to manifold 66 to conduit 70 (and to conduit 78 to close off anti-lockup valve) from conduit 70 to flow body 130 and thus to the patient.

Releasing the manual button will repressurise conduit 80 and close off main switch 32.

Thus in the manual mode of operation the operator will first of all rotate the slider 18 to the position where it does not register with any of the orifices 146. The operator will then place the mask over the face of the patient, and will manually operate the button, so as to supply pulses of breathable gas, at intervals, to the patient.

During the manual mode the auto shut-off valve will continue to operate but has no effect on manual operation, regardless of operation of the manual button. During manual ventilation, the demand mode can take place independent of the operator, and depends only upon the inspiratory effort of the patient.

Anti Lock-up Valve 46

The anti lock-up valve 46 (FIG. 4A) is mounted on the side wall of housing 130, giving access to flow body 36, It is connected, as previously noted, by conduit 78 to manifold 66.

Consequently, it is subjected to gas pressure only when main switch valve 32 is open, communicating gas from conduit 60 to conduit 64.

When main switch 32 is closed shutting off conduit 64, no pressure is supplied via conduit 78, to anti lock-up valve 46.

Anti lock-up valve 46 is comprised of a housing 166 open to atmosphere at 167.

Within housing 166 there is located a moveable piston 168, biased to the left into an open position by spring 170.

Flapper outlet valve 172 is adapted to open outwardly with respect to housing 130, allowing venting of any gas pressure within housing 130, during exhalation, and prevents ambient air being drawn into housing 130 during demand breathing by the patient.

Piston 168 responds to supply of gas pressure from conduit 64 and main switch 32 to move to the right and close against its seat, closing off the outlet from the housing 166.

Thus during the supply of gas from main switch 32 and conduit 64 to nozzle 72, the anti lock-up valve 46 and the flapper 172 are closed.

When the main switch 32 is shut off, and gas pressure is no longer supplied to conduits 64 and 78, then piston 168 moves back under pressure from spring 170, and any pressure within housing 130 can be relieved through valve 172 and housing 166, to atmosphere.

Demand Valve 42

The demand valve 42 (FIGS. 7A and 7B) will be seen to comprise an upper shell housing 180, fitted to the top of flow body 130.

Within housing 180 and flow body 130 there is provided a valve body 182, having outlet openings 184 therein. A pressure relief opening 186 is normally closed by a spring loaded pressure relief valve disc 188, which can lift off opening 186 is the event of an overpressure within housing 130. Opening 186 defines a lower valve seat 189.

Pressure relief openings 190 are formed in shell housing 180, to vent excess pressure to atmosphere.

Within the valve body 182, there is supported a diaphragm valve ring 192. Ring 192 is formed integrally with a flexible annular diaphragm ring 194, and inner integral groove ring 196. Groove ring 196 supports a circular spider valve member 198, which defines a plurality of pressure relief openings (not shown) spaced radially therearound. A flexible flapper valve 200 is secured to ring 198, and is adapted to flex upwardly to allow pressure relief from within body 130, but prevents inflow of any exterior gases.

Bleed orifice 162 which communicates with conduit 62 supplies gas pressure to a bleed nozzle 202, within demand valve 42.

Bleed nozzle 202 is normally closed by means of a closure pad 204 (FIG. 7A). Closure pad 204 is located at the free end of a flexible pivot arm 206, connected to spider 198. Pivot arm 206 is mounted on pivot shaft 207. The right hand end of arm 206 is normally urged upwardly by means of spring 208 forcing pad 204 downwardly. An adjustment lever 210, assists in controlling the upward and downward movement of lever 206.

Grooved ring portion 196 will also be urged upwardly against annular seat 189 off body 186 by spring 208 and arm 206, thereby closing off any escape of gas pressure through flapper valve 200, other than through pressure regulator disc 188.

The pressure of disc 188 can be preset to a desired operating overpressure, within the safe limits of the lung capacity of a patient.

The pressure within the portion of the demand valve 42 below the diaphragm valve 192 will normally be equal to the pressure of the breathable gas within the flow body 130. However, the demand valve 42 is separated from the rest of the flow body 130 by means of the annular wall 212. Wall 212 has a central gas flow opening 214 connecting with conduit 62. Around opening 214 there is a valve seat 216. A flexible valve closure disc 218 is adapted to seat on seat 216, and may flex upwardly off it.

The upper side of valve disc 218 communicates with the chamber 164, communicating with the bleed orifice 162.

The area around seat 216 below valve disc 218 is communicated by means of via passageways 220 (FIGS. 7A & 7B) to demand conduit 139, and thus connects downwardly into valve chamber 133.

Thus, when valve disc 218 lifts off seat 216 gas will flow from conduit 62, through opening 214 around seat 216 down through passageways 220 and conduit 139 and into flow body 130.

In non-demand operation, gas pressure will normally supplied from conduit 62 via bleed orifice 162 and bleed nozzle 202, to chamber 164.

Gas pressure will also be supplied via conduit 62, to opening 214.

Thus gas pressure on both sides of valve disc 218 will be the same. Consequently valve disc 218 will remain seated on seat 216.

However, when a patient makes an inspiratory effort, (FIG. 7B) then gas pressure within demand conduit 139 will drop and this will cause diaphragm ring 194 to flex downwardly, and this will in turn swing arm 206 and raise valve pad 204 up off bleed nozzle 202.

The pressure drop created by the inspiratory effort of the patient is communicated via suction tube 222, to demand valve 42.

The gas pressure within chamber 164 will thus drop, and valve 218 will rise upwardly due to the pressure within conduit 62 and chamber 214.

Gas will thus flow through opening 214 around seat 216 and down through passageways 220 into demand conduit 139.

Patient will thus be able to freely breathe gas supplied via conduit 62.

As previously explained, at the same time, when gas pressure within chamber 164 drops, piston 156 of auto shut-off valve 44 will be free to move to the right, and this will therefore supply gas pressure from conduit 58 and via conduit 86 to piston 120 of timing shuttle 34 (FIGS. 2 & 3).

This will therefore cause valve 118 to rise. This will in turn supply gas pressure to conduit 68 causing main switch 32 to close. Gas pressure will then no longer be supplied via conduit 64, and the timed pulsing of main switch 32 and timing shuttle 34 will cease.

As previously explained however, once the patient ceases to make an inspiratory effort, then valve disc 218 will close on seat 216, and valve pad 204 will swing down and close nozzle 202. Pressure will be equalized on opposite sides of valve disc 218, so that gas can no longer flow from conduit 62.

At the same time, auto shut-off valve 44 will move to the left. This will then shut off gas pressure to piston 120 of the timing shuttle 34. Pressure within timing shuttle 34 decays. This will then release the gas pressure in conduit 68, and main switch 32 can then rise upwardly. Timed pulses of gas will then be supplied via conduit 64 to conduit 138.

This will then cause timed operation of the timing shuttle 34 and main switch 32, so as to supply timed pulses of gas automatically to conduit 138.

Thus the demand valve 42 responds to inspiratory effort of the patient, or to lack of such effort, and in turn controls the operation of the timing shuttle and the main switch.

Changeover from automatic mode, to demand mode is therefore entirely dependent upon the efforts of the patient, or lack of them, and will not be dependent upon the skill or knowledge of the operator.

Figure 8:
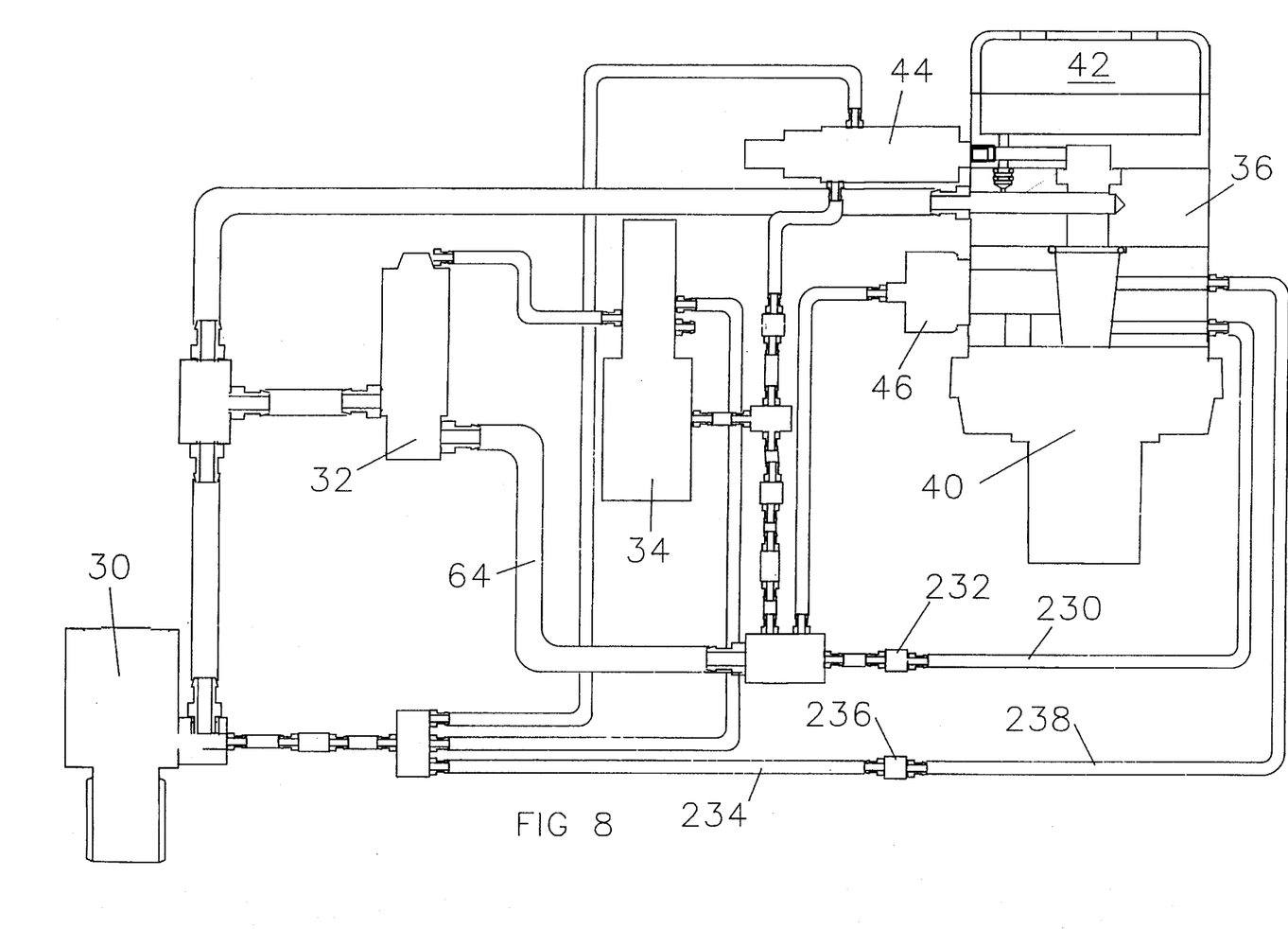
FIG. 8 is a schematic illustration of alternate embodiment.

An alternate embodiment of the invention is shown in FIG. 8, in which the flow control rotor 142 is eliminated. The modified form of the invention comprises a pressure regulator 30, a main control switch 32, a timing shuttle valve 34, and a flow body 36. The flow body 36 has a diaphragm 40, a demand valve 42, and an automatic shut-off valve 44, and anti-lockup valve 46, all substantially as described above.

In place of the flow control rotor 38 there is a flow supplied through fixed flow restrictor 232, to timing shuttle 34.

As before, gas is supplied from the main supply valve 32 via conduit 64.

Main supply valve 32 is cycled on and off by means of timing shuttle 34. Thus gas supply through conduit 230 will be in timed cycled pulses.

In this simplified form of the invention, a continuous bleed flow of gas is supplied via conduit 234, flow restrictor 236, and conduit 238 to flow body 36.

Thus in this form of the invention, while cycled pulses of gases are supplied through conduit 230, in the automatic mode, a continuous bleed flow of gas is also supplied via conduit 238, simultaneously.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. An automatic resuscitation apparatus for administering a breathable gas free of ambient air and pollutants to a patient said apparatus being adapted to be held in one hand and being selectively operable in either automatic mode, demand mode, or manual mode, said apparatus comprising;

a flow body having a flow conduit for a breathable gas;

a valve chamber and chamber valve means within said chamber connecting with said conduit for permitting passage of breathable gas from said chamber to a mask;

exhaust means for exhausting exhaled breath exteriorly of said chamber;

means for supplying breathable gas free of ambient air and pollutants to said flow body;

a switch valve operable to provide an on-off control of said breathable gas supply;

timing valve means responsive to flow of gas to said flow body, to move to an fro between on/off positions, at intervals corresponding to natural breathing cycle of a patient, said timing valve means being connected to said switch valve, whereby to procure on-off operation of said switch valve in timed relation to said timing valve means whereby said switch valve moves between on and off positions at the same said cycle as said timing valve means;

a flow control nozzle;

gas flow regulator control port means comprising a plurality of separate gas flow regulator orifices of varying sizes, moveably mounted in relation to said flow control nozzle and a selected one of said orifices being adapted to be selectively registered with said flow control nozzle for selecting a predetermined gas flow rate;

a manual gas flow control orifice adjacent said plurality of regulator orifices;

manual control means operable to select either said automatic mode, said demand mode, or said manual mode, said manual mode being selectable by manually moving said manual control so that said plurality of regulator flow control orifices are out of registration with said control nozzle, and, housing means adapted to beheld in one hand and enclosing said flow body, said valve chamber, said exhaust means, said switch valve, said timing valve means, said control nozzle, and said regulator control port means.

2. An automatic resuscitation apparatus as claimed in claim 1 wherein said timing valve means comprises a housing, a piston moveable to and fro within said housing, a valve connected to said piston, and a spring normally urging said piston in one direction, and being responsive to gas pressure to move against said spring, said timing valve means being connected to said switch valve.

3. An automatic resuscitation apparatus as claimed in claim 1 wherein said flow control port means comprises a disk member located in said chamber, a plurality of first flow openings located spaced radially from one another on one part of said disk member, a plurality of flow restricting orifices in said disk member radially spaced apart from one another, respective ones of said flow openings and restricting orifices being arranged in pairs in opposition to one another on said disk, flow nozzle means adapted to register with one of said flow openings, said control nozzle being adapted to register with a selected one of said orifices, and manually operable means for rotating said disk member relative to said control nozzle.

4. An automatic resuscitation apparatus as claimed in claim 1 wherein said exhaust means are defined by openings formed around said means for connecting a patient mask to said flow body, and wherein said chamber valve means comprises a generally annular wall portion, and an inner ring portion, and an annular diaphragm portion extending between said annular wall portion and said inner ring portion, for covering said exhaust openings, and further including a one-way outflow valve member supported within said inner ring means, and adapted to permit flow of breathable gas from said chamber valve means into said patient mask connection means.

5. An automatic resuscitation apparatus as claimed in claim 1 and including a pressure relief valve communicating with said flow body, and piston means operable to hold said relief valve closed during supply of breathable gas to said valve chamber, and spring means normally urging said piston means away from said valve.

6. An automatic resuscitation apparatus as claimed in claim 1 wherein said switch valve comprises a valve housing, a piston moveable within said housing, a spring normally urging said piston in one direction, gas opening means in said housing supplying pressurized gas to said piston, causing same to move against said spring, and a valve connected to said piston and operable to move in response to movement of said piston, and gas inlet and gas outlet conduits connected to said housing, and controlled by movement of said valve.

7. An automatic resuscitation apparatus as claimed in claim 6 including said switch valve, for transmitting pressurized gas to said flow body, and for also supplying pressurized gas to said timing valve means, and gas flow control orifice means for controlling flow of gas from said switch valve to said timing valve means.

8. An automatic resuscitation apparatus as claimed in claim 1 including a demand valve connecting with said flow body, and a demand gas flow conduit operable to supply gas to said demand valve, said demand valve being normally closed, and said demand valve being responsive to a predetermined drop in pressure in said flow body to open and to permit flow of gas into said chamber from said demand flow conduit.

9. An automatic resuscitation apparatus as claimed in claim 8 and including shut-off valve means moveable between on and off positions and connected to said demand valve and being operable to move said timing valve means and said switch valve into their off positions.

10. An automatic resuscitation apparatus as claimed in claim 9 and including anti lock-up valve means communicating with said flow body, and being normally closed during automatic mode, and being operable to provide additional exhaust during operation of said demand valve in said demand mode.

* * * * *